United States Patent [19]

Elliott et al.

[11] Patent Number: 4,777,185
[45] Date of Patent: Oct. 11, 1988

[54] PHENYL PHENOXYPHENYL PROPENYL CYCLOPROPANE PESTICIDES

[75] Inventors: Michael Elliott, Stevenage; Norman F. Janes, Luton; Bhupinder P. Singh Khambay, Harrow Weald; Ahmet Baydar, Harpenden, all of England

[73] Assignee: National Research Development Corporation, England

[21] Appl. No.: 720,374

[22] Filed: Apr. 5, 1985

[51] Int. Cl.$^4$ .................. C07C 43/205; C07C 43/21; A01N 31/14; A01N 31/16
[52] U.S. Cl. .................................. 514/719; 549/433; 549/445; 558/426; 568/637
[58] Field of Search ................. 568/637; 514/719; 558/426; 549/433, 443, 445

[56] References Cited

U.S. PATENT DOCUMENTS

| | | |
|---|---|---|
| 4,073,812 | 4/1978 | Bull et al. |
| 4,242,357 | 12/1980 | Fuchs et al. ............... 568/637 X |
| 4,562,213 | 12/1985 | Nishido et al. ............ 568/637 X |
| 4,611,004 | 9/1986 | Ackermann et al. ........ 514/719 X |

FOREIGN PATENT DOCUMENTS

| | | |
|---|---|---|
| 0094085 | 5/1983 | European Pat. Off. |
| 222730 | 6/1985 | Japan |
| 242532 | 7/1985 | Japan |
| 1570982 | 7/1980 | United Kingdom |
| 2085006A | 10/1981 | United Kingdom |
| 2120664A | 12/1983 | United Kingdom |

OTHER PUBLICATIONS

Recent Advances in the Chemistry of Insect Control, The Royal Society of Chemistry, pp. 72–91.
Rothamsted Experimental Station, pub. Jun. 1985, pp. 102–103.
Structural Requirements for Phrethrin–Like Activity, M. Elliot, 1969, pp. 776–781.
Lipophilic Insect Control Agents, Michael Elliott.
Chem. Abstracts 99: 135477A, Oxime Ether Phrethroids and Hydroxylamine Ether Propyrethroids.
Chem. Abstracts 99: 122008y, Benzyl Propyl Ethers.
Chem. Abstracts 99: 11787u, Acaricidal and Insecticidal Composition.
Chem. Abstracts 99: 83735m, Acaricidal and Insecticidal Composition.
Chem. Abstracts 99: 53343q, 3-Phenoxybenzyl 2-(4-ethoxyphenyl)-2 -methylpropyl Ether.
Chem Abstracts 99: 48961K, Pesticide Composition for Carbamate Resistant Insects and Mites.
Chem. Abstracts 99: 99: 48962m, Insecticidal and Acaricidal Composition.
Chem. Abstracts 99: 34536p., Arylelthyl Ethers as Acaaricides and Insecticides.
Chem. Abstracts 99: 18111r, Insecticidal and Acaricidal Composotion.
Chem. Abstracts 98: 143123b, Para-methylacetophenone.
Chem. Abstracts 97: 72116t, Insecticidal Phenoxybenzyl carbamates.
Chem. Abstracts 99: 122005v, Arylpropyl Phenoxybenzyl Ethers.
Chem. Abstracts 99: 139486a, 2-Arylpropyl Ethers.
Chem. Abstracts 99: 158010g, 3-Phenoxy-4-fluorobenzyl 2-(4-Ethoxyphenyl)-2-methylpropyl ether.
Chem. Abstracts 97: 181951g, 2-Aminopropanol Derivatives.
Chem. Abstracts 97: 181951g, 2-Aminopropanol Derivatives.
Chem. Abstracts 94: 1075f, Ketone Insecticides.
Chem. Abstracts 29312z, Fungicidal 2,2-Didhalocyclopropane Derivatives.
Abstract of the Reports Made by Researcher of Mitsui Toatsu at the Annual Meeting of Pesticide Science Society of Japan (1984).

*Primary Examiner*—J. E. Evans
*Attorney, Agent, or Firm*—Jacobs & Jacobs

[57] ABSTRACT

Pesticidal compounds of formula I

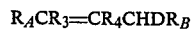

$$R_4CR_3=CR_4CHDR_B \qquad I$$

in which formula:
$R_A$ represents a group $ArCR_1R_2$—in which Ar represents a phenyl or naphthyl group optionally substituted by one or more halogen, alkoxy, haloalkoxy, methylenedioxy, $C_1$–$C_6$ alkyl or haloalkyl groups;
$R_1$ and $R_2$ together with the carbon to which they are attached represent a $C_3$–$C_6$ cycloalkyl group optionally substituted by one or more halogen atoms or $C_1$–$C_6$ alkyl groups.
$R_3$ and $R_4$ which may be identical or differ, represent hydrogen halogen or $C_1$–$C_6$ alkyl groups and
$R_B$ represents the residue of an alcohol $R_B$ CHDOH in which D is hydrogen or cyano and of which the [1R, cis]2,2-dimethyl-3-(2,2-dibromovinyl) cyclopropane carboxylic ester is significantly insecticidal,
the configuration of $R_A$ and $CHDR_B$ about the double bond being mutually trans,
and processes for the production of compounds I, intermediates, pesticidal compositions comprising I, processes for the production thereof, methods for controlling pests, especially rice pests, in which such compounds are utilized and the use of compounds I for the manufacture of a pesticide.

21 Claims, No Drawings

PHENYL PHENOXYPHENYL PROPENYL CYCLOPROPANE PESTICIDES

This invention relates to pesticides and in particular to pesticidal compounds, the production of such compounds, intermediates for use in their production, compositions containing such compounds and the use of such compounds and compositions for pest control.

Compounds have now been discovered formulations of which, whilst effective against a range of insect and other pests, are of particular interest for the control of infestation in rice crops.

Accordingly the present invention comprises a compound of formula I $$R_A CR_3 = CR_4 CHDR_B$$

in which formula:

$R_A$ represents a group $ArCR_1R_2$— in which Ar represents a phenyl or naphthyl group optionally substituted by one or more halogen, alkoxy, haloalkoxy, methylenedioxy, $C_1$–$C_6$ alkyl or haloalkyl groups;

$R_1$ and $R_2$ together with the carbon to which they are attached represent a $C_3$–$C_6$ cycloalkyl group optionally substituted by one or more halogen atoms or $C_1$–$C_6$ alkyl groups.

$R_3$ and $R_4$ which may be identical or differ, represent hydrogen, halogen or $C_1$–$C_6$ alkyl groups and $R_B$ represents the residue of an alcohol $R_B CHDOH$ in which D is hydrogen or cyano and of which the [1R, cis]2,2-dimethyl-3-(2,2-dibromovinyl)cyclopropane carboxylic ester is significantly insecticidal, the configuration of $R_A$ and $CHDR_B$ about the double bond being mutually trans.

Although, desirably, methods for producing compounds I are such that the product is free from the structural isomer of formula II:

$$ArCR_1R_2CR_3HCR_4 = CDR_B \qquad II$$

certain methods may give rise to a product contaminated with the isomer.

Although compound I is preferably substantially free from compound I being contaminated by less than 10% and usually less than 1% thereof on a molar basis, higher levels of contamination may be tolerated, though it is unusual for more than 50% of compound II to be present.

Ar, is typically substituted phenyl and substitution is usually at the 3-(meta) and/or 4-(para)-position by fluorine, bromine, chlorine, a $C_1$–$C_6$ alkyl group e.g. methyl or tertbutyl, a $C_1$–$C_6$ alkoxy group e.g. methoxy, ethoxy, a halomethoxy or haloethoxy group, which may comprise one or more halogens, e.g. $OCF_3$, $OCF_2H$ or halomethyl or haloethyl group e.g. $CF_3$. Ar generally carries no more than two substituents, and typically only one.

The substituents $R_1$ and $R_2$, together with the carbon bearing them, typically represent a substituted or unsubstituted cyclopropyl group which, when substituted, preferably carries halogen and especially fluorine as in 2,2-difluorocyclopropyl.

When the compound of formula I is chiral (as in the immediately foregoing case) it can of course exist in different stereoisomeric forms. Both mixtures of stereoisomers and single stereoisomers are included within the scope of the present invention.

One or each of $R_3$ and $R_4$ typically represents hydrogen. When, however, one or both represent halogen, and in particular bromine chlorine or fluorine, fluorine is usually preferred.

$R_B CHD$ may represent the residue of an alcohol of formula $R_B CHDOH$ claimed or described in the specification for UK Pat. No. 1413491 which gives rise to significant insecticidal activity when esterified with [IR, cis]-2,2-dimethyl-3-(2,2-dibromovinyl)carboxylic acid. Potency towards houseflies is usually at least 5 relative to bioresmethrin=100 and may be 10 or more.

Typically $R_B CHD$ represents the residue of an alcohol $R_B CHDOH$ which is a phenoxy, benzyl or benzoyl substituted benzyl alcohol. 3-Phenoxybenzyl and 4-fluoro-3-phenoxybenzyl residues are of particular interest.

The present invention includes within its scope a process for the production of a pesticide compound in which a compound comprising a moiety $R_A$ and a compound comprising a moiety $R_B$ are reacted together forming the link —$CR_3 = CR_4 CHD$— between $R_A$ and $R_B$ in the product of formula I: $R_A CR_3 = CR_4 CHDR_B$. Typically the link is formed by a reaction of a known class.

Compounds of Formula I may be produced by a preferred process within the scope of the present invention, in which the product of a sterically hindered organoborane with a compound of formula $R_A C \equiv CH$ is catalytically coupled to a compound of formula $R_B CHDX$, the resultant reaction mixture being treated with an oxidising agent prior to isolation of the product of formula I. Typically, the organoborane is a sterically hindered mono or dialkyl borane e.g. disiamyl, dicyclohexyl, thexyl borane or is catechol borane, which is reacted with the ethynyl compound of formula $R_A$-$C \equiv CH$ to give a product which is coupled to the compound of formula $R_B CHDX$ (in whih X represents halogen, e.g. bromine) in the presence of a palladium(O) catalyst e.g. trikis—or tetrakis(triphenylphosphine)-palladium(O). The oxidising agent added may be alkaline e.g. alkaline hydrogen peroxide. Palladium(O) catalysis is described in Tsuji, J., Organic Synthesis with Palladium Compounds, Pub. Springer-Verlag, Berlin, 1980 and this type of coupling reaction is described in Miyaura et al, Tetrahedron Letters Vol. 21 pp. 2865-2868. The production of sterically hindered boranes is described in Brown, H. C. Organic Syntheses via Boranes, J. Wiley & Sons, N.Y. 1975 Ch. III. Sterically hindered mono- and dialkyl boranes may be produced by reaction of a complex of borane and e.g. dimethyl sulphide, tetrahydrofuran or an amine for example a tertiary amine with a suitable alkene, such as in the case of disiamyl broane, 2-methyl-2-butene.

The procedure is shown in the following simplified scheme:

$$ArCR_1CR_2CH_2OH \rightarrow ArCR_1R_2.CHO \rightarrow ArCR_1R_2CH=CBr_2 \rightarrow ArCR_1R_2C \equiv CH + R_B CHDX \rightarrow ArCR_1R_2.CH \equiv CH.CHDR_B$$

Intermediates of formula $ArCR_1R_2C \equiv CH$ and complexes thereof with sterically hindered mono or dialkyl boranes or catechol borane and products of the compound $R_B CHDX$ with a palladium(O) catalyst e.g. tetrakis(triphenylphosphine)palladium(O) are within the scope of the present invention.

In an alternative process within the scope of the present invention for producing a compound of formula I, a nucleophilic species of formula $R_B^-$ is catalytically reacted with:

(i) a compound of formula $R_4CR_3(CR_4=CH_2)OR$
or
(ii) a compound of formula $R_4CR_3\overset{t}{=}CR_4CHDQ$,
in which formulae
$R_4$ $R_3$ and $R_4$ are as hereinbefore described, and
OR and Q represent good leaving groups.

Typically, the reaction is carried out in the presence of a transition metal catalyst which is preferably a copper salt or a complex thereof with a lithium salt The nucleophilic species $R_B^-$ is generally present in the form of a Grignard reagent of formula $R_BMgBr$ or an alkali metal compound e.g. $R_BLi$, and the leaving group is typically acyloxy e.g. acetoxy or tosyloxy especially when representing OR, in case (i) or halogen e.g. bromine or acyloxy particularly when representing Q in case (ii). The copper salt is usually cuprous and a halide e.g. a bromide or iodide or a cyanide, and the complex of formula $Li_2CuY_2Z_2$ whein Y & Z represent chlorine, bromine, iodine or cyano. Transformations of type (ii) are described by E. Erdick in Tetrahedron, 1984, 40, 641-657.

The following route illustrates a typical procedure, the transformation (b) of which is analagous to one described in Tetrahedron Letters 1982, 4669.

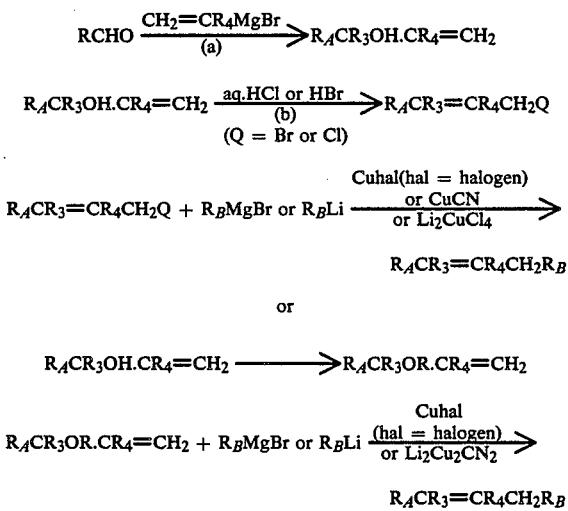

In the foregoing reaction scheme $R_4$ typically represents 4-chlorophenyl or 4-ethoxyphenyl, $R_3$ and $R_4$ hydrogen, Q bromine and $R_B$ 3-phenoxyphenyl or 4-fluoro-3-phenoxyphenyl.

Intermediates of formula $R_4CR_3=CR_4CHDQ$, $R_4CR_3OR,CR_4=CH_2$ and $R_4CR_3OHCR_4=CH_2$ are also within the scope of the present invention.

In a yet further process within the scope of the present invention for the production of a compound I, an alcohol of formula $R_4CR_3=CR_4CHOHR_B$ is reduced, typically with a mixture of a trialkylsilane, such as triethylsilane, with a complex of boron trifluoride such as boron trifluoride etherate (e.g. diethyl etherate). Separation from the contaminating isomer $R_4CR_3HCR_4=CDR_B$ may be desirable or requisite. Typically $R_3$ $R_4$ and D represent hydrogen.

Compounds of formula $R_4CR_3=CR_4CDOHR_B$ may be produced, in accordance with the further aspect of the present invention, by treatment of compounds of formula $R_4CR_3=CR_4COR_B$ with a mild reducing agent, typically a mild hydride reducing agent such as sodium borohydride.

Intermediates of formula $R_4CR_3=CR_4CDOHR_B$ are further included within the scope of the present invention, $R_3$, $R_4$ and D typically representing hydrogen.

Compounds of formula I can be used to combat pest infestation in the domestic, horticultural or agricultural or medical, including veterinary, areas.

The present invention also includes within its scope a process for the production of a pesticidal composition which comprises formulating a compound of formula I with an inert carrier or diluent and compositions thereby produced. The compound of formula I in the composition is normally contaminated by less than 50% on a molar basis of the isomer II $ArCR_1R_2CR_3HCR_4=CDR_B$ and is preferably substantially free therefrom.

Compositions may be in the form of dusts and granular solids, wettable powders, mosquito coils and other solid preparations or as emulsions, emulsifiable concentrates, sprays and aerosols and other liquid preparations after the addition of appropriate solvents, diluents and surface-active agents.

Agriculturally and horticulturally applicable compositions, which require the active ingredient to possess significant photostability are of particular interest and especially compositions which are acceptable for application to crops, such as rice, which are cultivated in environments in which fish are exposed to the compound I. It will be appreciated that fish safety is of great importance in such applications and that suitable compositions should contain no fish-toxic ingredients.

The pesticidal compositions of the invention normally contain from 0.001 to 25% by weight of the compound of formula I but the compositions can contain higher concentrations of active ingredient of formula I e.g. up to 95% in compositions to be sold as concentrates for dilution before use by the ultimate user.

The compositions of the invention can, depending on the intended application, include diluents such as hydrocarbon oils, e.g. xylene or other petroleum fractions, water, anionic, cationic or non-ionic surface-active agents, anti-oxidants and other stabilisers as well as perfumes and colouring matters. These inert ingredients may be of the type and in proportions such as are conventionally used in pesticidal compositions containing pyrethroid-like compounds.

In addition to these inactive ingredients, the compositions of the present invention may contain one or more further active ingredients which may be other pesticidal compounds of the pyrethroid type or of other types and the composition may also include synergists particularly those of a type known to be capable of synergising the activity of natural pyrethrin and pyrethroid-like insecticides. Synergists of this type include piperonyl butoxide, tropital and sesamex.

Compounds of formula I may be applied in such a manner that pest infestation is diminished or prevented or both.

In accordance with a further aspect of the present invention, a method of pest control comprises treating a pest or a surface or environment susceptible to pest infestation with an effective amount of a compound of formula I $$R_4CR_3=CR_4CHDR_B \qquad \qquad I$$

in which formula:

$R_A$ represents a group of formula $ArCR_1R_2$— in which Ar represents a phenyl or naphthyl group optionally substituted by one or more halogen, alkoxy, haloalkoxy, methylenedioxy, $C_1$-$C_6$ alkyl or haloalkyl groups.

$R_1$ and $R_2$ together with the carbon to which they are attached represent jointly a $C_3$-$C_6$ cycloalkyl group optionally substituted by one or more halogen atoms or $C_1$-$C_6$ alkyl groups;

$R_3$ and $R_4$, which may be identical or differ, represent hydrogen, halogen or $C_1$-$C_6$ alkyl groups;

$R_B$ represents the residue or an alcohol $R_BCHDOH$ in which D is hydrogen or cyano and of which the [IR, cis]2,2-dimethyl-3-(2,2-dibromovinyl)cyclopropane carboxylic ester is significantly insecticidal;

the configuration of $R_A$ and $CHDR_B$ about the double bond being mutually trans.

The compounds or compositions of the invention can be used as insecticides or acaricides for example in a domestic environment in spraying rooms to combat infestation with houseflies or other insects, they can be used for treatment of stored crops or cereals to combat infestation by insects or other pests, they can be used to spray growing crops, e.g. cotton to combat infestation by common pests and they can be used in the medical or veterinary field, e.g. as a cattle spray to prevent or treat infestation by insects or other pests.

It is envisaged, however, that the compounds and compositions of the present invention will be of especial interest for application to crops which are cultivated in environments in which fish are exposed to pesticides.

The present invention is of particular interest for controlling rice pests, particularly Chilo species such as *Chilo suppressalis*, the rice stem borer, *Nilaparvata lugens*, the brown plant hopper, *Nephotettix cincticeps*, the green rice leaf hopper and *Lissorhoptrus oryzophilus*, the rice water weevil. Other particular pests against which it is envisaged that the compounds and compositions of the present invention will find application include Blattella species such as *Blatella germanica*, the German cockroach, *Anthonomus grandis*, the Boll weevil, and Lepidopteran pests, particularly Lepidopteran pests other than Heliothis species such as Spodoptera species and especially *Spodoptera exigua*, the beet army worm.

The spectrum of effectiveness of the compounds of formula I is demonstrated by activity against mosquito larvae, houseflies, black bean aphids, red spider mite, and *Spodoptera littoralis*, especially against adult caterpillars. Ovicidal activity, including activity towards eggs of the red spider mite and of *Spodoptera littoralis* is of particular significance.

The present invention further includes within its scope the use of a compound of formula I for the manufacture of a pesticide, typically an insecticide or acaricide and in particular a pesticide for use in controlling rice pests.

The compounds are additionally of interest for the control of pests such as the following:

from the class of the Isopoda, for example *Oniscus asellus, Armadillidium vulgare* and *Porcellio scaber*;

from the class of the Diplopoda, for example *Blaniulus guttulatus*;

from the class of the Chilopoda, for example *Geophilus carpophagus* and Scutigera spec;

from the class of the Symphyla, for example *Scutigerella immaculata*;

from the order of the Thysanura, for example lepisma saccharine;

from the order of the Collembola, for example *Onychiurus armatus*;

from the order of the Orthoptera, for example *Blatta orientalis, Periplaneta americana, Leucophaea madarae, Acheta domesticus*, Cryllotalpa spp., *Locusta migratoria migratorioides, Melanoplus differentialis* and *Schistocerca gregaria*;

from the order of the Dermaptera, for example *Forficula auricularia*;

from the order of the Isoptera, for example Reticulitermes spp;

from the order of the Anoplura, for example *Phylloxera vastatrix*, Pemphigus spp., *Pediculus humanus corporis*, Haematopinus spp. and Linognathus spp;

from the order of the Mallophaga, for example Trichodectes spp. and Demalinea spp;

from the order of the Thysanoptera, for example *Hercinothrips fermoralis* and *Thrips tabaci*;

from the order of the Heteroptera, for example Eurygaster spp., *Dysdercus intermedius, Piesma quadrata, Cimex lectularius, Rhodnius prolius* and Triatoma spp;

from the order of the Homoptera, for example *Aleurodes brassicae, Bemisia tabaci, Trialeurodes vaporariorum, Aphis gossypii, Brevicoryne brassicae, Gryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Lecanium corni, Saissetia oleae, Laodelphax striatellus, Aondiiella aurantii, Aspidiotus hederae*, Pseudococcus spp. and Psylla spp;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis Chrysorrhoea*, Lymantria spp., *Bucculatrix thurberiella, Phyllocnistis citrella*, Agrotis spp., Euxo spp., Feltia spp., *Earias insulana, Laphygma exigua, Mamestra brassicae, Panolis flammea, Prodenia litura, Trichoplusia ni, Carpocapsa pmonella*, Fieris spp.,

*Pyrausta nubilalis, Ephestia kuehniella, Galleria mellonella, Cacoecia podana, Capua reticulana, Choristoneura fumiferana, Clysia ambiguella, Homona magnanima* and *Tortris viridana*;

from the order of the Coleoptera, for example *Anobium punctatum, Thizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Sitophilus spp., *Otiorrhynchus sulcatus, Cosmoplites sordidus, Geuthorrhynchus assimilis*, Hyperapostica, Dermestes spp., Trogoderma spp., Anthrenus spp., Attagenus spp., Lyctus spp., Meligethes aeneus, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*;

from the order of the Hymenoptera, for example Diprion spp., Hoplacampa spp., Lasius spp., *monomorium pharaonis* and Vespa spp., from the order of the Diptera, for example Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp.,

*Bibio hortulanus,* Oscinella frit, Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The invention is illustrated by the following Examples:

Temperatures are in °C. and refractive indices are measured at 20° C.

EXAMPLE 1

1-(4-chlorophenyl)-1-(E-3-(phenoxyphenyl)-prop-1-enyl)-cyclopropane

A. 1-(4-chlorophenyl)-1-cyclopropanemethanal (Compound a)

A mixture of 1-(4-chlorophenyl)-1-cyclopropanemethanol (7 g) pyridinium dichromate (21.7 g) and dichloromethane (200 ml) is stirred overnight at room temperature. Petroleum ether b.p. 40°–60° C. (200 ml) is added and stirring continued for another 30 minutes. The mixture is filtered through a pad of celite and charcoal and the solvent is evaporated off under reduced pressure. The residue is distilled at 0.33 mm Hg and the main fraction, bp 73°–75° C. consists of the required aldehyde, yield 5.2 g, $n_D1.5532$.

B.

1-(4-chloropheny(-1-(2,2-dibromovinyl)-cyclopropane (Compound b)

To a stirred solution of dry carbon tetrabromide (11 g) in dry dichloromethane (200 ml) under nitrogen is added triphenylphosphine (17.4 g). After 15 minutes 1-(4-chlorophenyl)-1-cyclopropanemethanal (3 g) dissolved in dichloromethane (10 ml) is added. The mixture is stirred for 2 hours at room temperature, poured onto saturated ammonium chloride solution and extracted with petroleum ether b.p. 60°–80° C. (x3). The combined extracts are washed with water, dried and the solvent evaporated off under reduced pressure to give the required compound, yield 5.1 g, $n_D1.5976$.

C. 1-(4-chlorophenyl)-1-ethynylcyclopropane (Compound c)

To a stirred solution of 1-(4-chlorophenyl)-1-(2,2-dibromovinyl)-cyclopropane (1 g) in dry ether (50 ml) under nitrogen and cooled to −78° C., is added 1.6M n-butyllithium (3.7 ml) over 15 minutes whilst maintaining the temperature below −60° C. After stirring for a further 5 minutes, 2N aqueous hydrochloric acid (40 ml) is added and the mixture is allowed to warm up to room temperature. The mixture is extracted with ether (x3) filtered, dried and the solvent evaporated off under reduced pressure to give the required compound, yield 0.5 g $n_D1.5460$.

D.
1-(4-chlorophenyl)-1-(E-3-(3-phenoxyphenyl)-prop-1-enylcyclopropane (Compound 1)

To a stirred solution of 2-methyl-2-butene (0.5 ml) in dry ether (2 ml) under nitrogen at 0° C., is added borane-methyl sulphide complex (1.15 ml of 2M solution in ether) and the mixture stirred for 1 hour. A solution of 1-(4-chlorophenyl)-1-ethynylcyclopropane (0.4 g) in ether (5 ml) is added in one portion, stirred for 10 minutes and then allowed to warm to room temperature over 1 hour. The ether is then evaporated off at reduced pressure and the residue dissolved in dry benzene (10 ml) and kept under nitrogen.

In another flask, tetrakis (triphenylphosphine)palladium(O) (0.1 g) is stirred under nitrogen in dry benzene (10 ml) and a solution of 3-phenoxyphenyl bromide (0.6 g) in dry benzene (10 ml) added over 10 minutes. To this mixture is then added the reagent prepared above followed by 2M aqueous sodium hydroxide (2.3 ml) and the mixture is refluxed for about two hours. After cooling 3Maq. sodium hydroxide (1 ml) is added followed by 30% $H_2O_2$ (1 ml). After cessation of the exothermic reaction, the reaction mixture is stirred at room temperature for half an hour, poured onto water, and extracted with ether (x3). The combined extracts are washed with water, dried and the solvennt removed under reduced pressure. The product is isolated by thin layer chromatography on silica eluting with neat petroleum ether b.p. 40°–60° C. to yield 0.41 g, $n_D1.5988$.

EXAMPLES 2–11

The following aldehydes are prepared as described in Example 1(A:)

d. 1-(3,4-methylenedioxyphenyl)-1-cyclopropane methanol, $n_D^{20}1.5545$ e. 1-(4-ethoxyphenyl)-2,2-difluoro-1-cyclopropane methanal, $n_D^{20}1,5063$ The precursor for compound e is prepared as follows:

1-(4-ethoxyphenyl)-2,2-difluorocyclopropane-1-methanol

To 1.0 g of lithium aluminium hydride in 120 ml of dry ether, at room temperature is added dropwise 5.4 g (0.02 moles) of ethyl-1-(4-ethoxyphenyl)-2,2-difluorocyclopropane-1-carboxylate in 20 ml of ether. The reaction mixture is stirred for 1 hr after which 1.0 ml of water 1.0 ml of 15% NaOH, followed by 3.0 ml of water are added. The solid precipitate is filtered off, washed with ether and the combined filtrates dried and concentrated under reduced pressure to yield (4.2 g) a colourless oil; $n_D1.5129$.

1-(4-ethoxyphenyl-1-cyclopropanemethanal (Reference f) is prepared as follows:

1-cyano-1-(4-ethoxyphenyl)cyclopropane

To 7.5 ml (0.012 mol) of 1.7M n-butyllithium in hexane, at room temperature, under an atmosphere of nitrogen, is added rapidly 10 ml of anhydrous tetrahydrofuran, followed by a solution of 4-ethoxyphenyl acetonitrile (0.8 g 0.005 mol) in 4 ml of tetrahydrofuran, during 5 minutes. The reaction mixture is stirred magnetically for 1 hour then treated with 0.50 g (0.005 mol) of 1,2-dichloroethane in 10 ml of tetrahydrofuran, during a period of 40 minutes (slow addition is important). After 16 hours, the mixture is hydrolysed by 10 ml of 3N HCl and then taken up in ether, washed with water, sodium bicarbonate, water and dried over anhydrous sodium sulphate. The solvent is removed under reduced pressure. Yield: 0.64 g of a viscous semi-crystalline oil.

1-(4-ethoxyphenyl)-1-cyclopropane methanal (Compound f)

To 0.625 g (0.0033M) of 1-cyano-1-(4-ethoxyphenyl)-cyclopropane in dry benzene (25 ml) and dry heptane (10 ml) at 0° C. under an atmosphere of nitrogen, diisobutylaluminium hydride in hexane (3.4 ml of 1M., 0.0033 mol) is added dropwise via a hypodermic syringe The mixture is stirred at 0° C. for 3 hours, then allowed to warm to room temperature, poured onto saturated ammonium chloride and ice and is acidified with dil. $H_2SO_4$ then extracted with ether. The ethereal layer is washed with saturated sodium bicarbonate, saturated sodium chloride, and dried. The solvent is removed under reduced pressure and the aldehyde is purified by column chromatography on florisil with petroleum ether (b.p. 60°-80° C.) as eluant. Yield: 0.42 g ($n_D$: 1.5342).

The above aldehydes are coverted to the corresponding dibromovinyl compounds by following the method of Example 1(B) to give:

Compound
g: 1-(2,2-dibromovinyl)-1-(4-ethoxyphenyl)cyclopropane, $n_D^{20}$1.5976
h: 1-(2,2-dibromovinyl)-1-(3,4-methylenedioxyphenyl)-cyclopropane, $n_D^{20}$1.5970
i: 1-(2,2-dibromovinyl)-1-(4-ethoxyphenyl)-2,2-difluorocyclopropane, $n_D^{20}$1.5433

The following acetylenes are prepared by following the method of Example 1(C):

Compound
j: 1-(4-ethoxyphenyl)-1-ethynylcyclopropane, $n_D^{20}$1.5325
k: 1-(3,4-methylenedioxyphenyl)-1-ethynylcyclopropane, $n_D^{20}$1.5569
kk: 1-(4-ethoxyphenyl)-1-ethynyl-2,2-difluorocyclopropane, $n_D^{20}$1.5170

The following olefins are prepared by following the method of Example 1(D):

Compound
2. 1-(4-chlorophenyl)-1-(E-3-(4-fluoro-3-phenoxyphenyl)-prop-1-enyl)-cyclopropane, $n_D^{20}$1.5805
3. 1-(4-ethoxyphenyl)-1-(E-3-phenoxyphenyl)-prop-1-enyl)-cyclopropane, $n_D^{20}$1.5837
4. 1-(4-ethoxyphenyl)-1-(E-3-(4-fluoro-3-phenoxyphenyl)-prop-1-enyl)-cyclopropane, $n_D^{20}$1.5799
5. 1-(3,4-methylenedioxyphenyl)-1-(E-3-(3-phenoxyphenyl)-prop-1-enyl)-cyclopropane, $n_D^{20}$1,5969
6. 1-(3,4-methylenedioxyphenyl)-1-(E-3-(4-fluoro-3-phenoxyphenyl)-prop-1(E)-enyl)-cyclopropane $n_D^{20}$1.5886
7. 1-(4-ethoxyphenyl)-1-(E-3-(3-phenoxyphenyl)-prop-1-enyl-2,2-difluorocyclopropane, $n_D^{20}$1.5763
8. 1-(4-ethoxyphenyl)-1-(E-3-(4-fluoro-3-phenoxyphenyl)-prop-1-enyl)-2,2-difluoropropane, $n_D^{20}$1.5689

For production of compounds 7 and 8 the method of Example 1(D) is modified by diminishing the time the reaction mixture is exposed to alkaline hydrogen peroxide to five minutes.

EXAMPLE 9

A.
1-(4-chlorophenyl)-1-(E-3-(3-phenoxyphenyl)-prop-1-en-3-onyl)-cyclopropane (Compound m)

A mixture of 1-(4-chlorophenyl)-1-cyclopropane methanal 1.80 g (0.01M), 3-phenoxy-acetophenone 2.12 g (0.01M), and 3.0 g of potassium hydroxide in 25 ml of ethanol is stirred at room temperature for 2 hours. The reaction mixture is poured into 200 ml of water and extracted with ether. The ether extract is washed with water, dried and the solvent is removed under reduced pressure to give 4.1 g of crude 1-(4-chlorophenyl)-1-(E-3-(3-phenoxyphenyl)-prop-1-en-3-onyl)cyclopropane, which is purified by column chromatography on 100 g of florisil (eluant: petroleum ether (b.p. 60°-80° C.) and ethyl acetate: 9/1) to give 3.04 g of the pure product, $n_D$1.5943

B.
1-(4-chlorophenyl)-1-(E-3-(3-phenoxyphenyl)-prop-1-enyl)-cyclopropane and 1-(4-chlorophenyl)-1-(E-3-(3-phenoxyphenyl)prop-2-enyl)-cyclopropane To 1.87 g (0.005M) of 1-(4-chlorophenyl)-1-(E-3-(3-phenoxyphenyl)-1-prop-1-en-3-onyl)-cyclopropane in 30 ml of ethanol is added 0.28 g (0.0075 mol, 1.5 mol eq.) of sodium borohydride and the mixture is stirred at room temperature for 3 hours. Water (20 ml) is then added, followed by dil HCl (25 ml) and the mixture is taken up in ether (150 ml). The ethereal layer is washed with sodium bicarbonate (x2) water (x3) and dried. The solvent is removed under reduced pressure to give the crude intermediate alcohol (1.88 g.)

The alcohol (1.88 g, 0.005 mol) and triethylsilane (0.87 g, 0.0075 mol, 1.5 mol eq) in 50 ml of dry dichloromethane are cooled using an acetone/solid carbon dioxide bath under an atmosphere of nitrogen. Dropwise addition of boron trifluoride etherate (0.77 g, 0.0055 mol.) gives a solution which is stirred until thin layer chromatography indicates that no alcohol is present and is then quenched by addition of ca. 15 ml of aqueous sodium bicarbonate. The cooling bath is removed and the solution allowed to warm to room temperature with vigorous stirring. The mixture is transferred to a separating funnel, ether (100 ml) is added and the whole washed with bicarbonate (50 ml) and water (x2). Drying and removal of the solvents affords an oil. Purification by column chromatography on florisil using petroleum ether (b.p. 60°-80° C.) as eluant yields 1.02 g of an oil, a 3:7 mixture of the two olefins. They are separated using petroleum ether (b.p. 40°-60° C.) as eluant by thin layer chromatography on silica, the plate being developed three times. 1-(4-chlorophenyl)-1-(E-3-(3-phenoxy-phenyl)prop-1-enyl)-cyclopropane ($n_D$: 1.5988, yield; 0.18 g, rf: 0.36 (Compound 1) and 1-(4-chlorophenyl)-1-(E-3-(3-phenoxyphenyl)-prop-2-enyl)-cyclopropane ($n_D$: 1.5686, yield:: 0.53 g, rf: 0.4) are both colourless viscous oils.

EXAMPLE 10

A.
1-(4-chlorophenyl)-1-(1-hydroxyprop-2-enyl)cyclopropane (compound n)

To a stirred solution of 1-(4-chlorophenyl)-1-cyclopropanemethanol (1.8 g) in dry tetrahydrofuran (60 ml) at −78° C. is added IM vinylmagnesium bromide (12 ml) in tetrahydrofuran over 10 mins. The mixture is then allowed to warm to −20° C. and saturated aqueous ammonium chloride added (30 ml). The mixture is concentrated under reduced pressure, and extracted with ether (x3). The combined extracts are dried and the solvent evaporated under reduced pressure to the required compound, 3 g, $n_D1.5523$.

B.
1-(4-chlorophenyl)-1-(E-3-bromoprop-1-enyl)cyclopropane (Compound O)

To a stirred solution of 1-(4-chlorophenyl)-1-(1-hydroxyprop-2-enyl)cyclopropane (2 g) in petroleum ether b.pt 60°–80° C. (100 ml) is added 48% aqueous hydrobromic acid (30 ml) whilst maintaining the temperature between −20° C. and −10° C. After ½ h, water (100 ml) is added and the mixture extracted with petroleum ether b.p. 60°–80° C. (x3). The combined extracts are washed with water, saturated sodium bicarbonate, dried and the solvent evaporated off under reduced pressure to give the required compound, 2.8 g, $n_D1.5678$.

C.
1-(4-chlorophenyl)-1-(E-3-(3-phenoxyphenyl)-prop-1-enyl)-cyclopropane

A Grignard reagent is prepared at 20° C. by reacting 3-phenoxyphenyl bromide (0.3 g) and dry magnesium turnings (0.26 g) in dry ether (4 ml) and cooled to −78° C. Cuprous bromide (0.03 g) is added followed by a solution of 1-(4-chlorophenyl)-1-(E-3-bromoprop-1-enyl)cyclopropane (0.28 g) in dry tetrahydrofuran (4 ml) added over 3 min. The mixture is stirred at −78° C. for 5 min and then allowed to warm to room temperature over 15 h. Saturated aqueous ammonium chloride solution (10 ml) is added and the mixture extracted with ether (x3), washed with water, dried and the solvent evaporated under reduced pressure. The residue is purified by thin layer chromatography, eluting with petroleum ether b.p. 60°–80° C. Yield 0.3 g.

Pesticidal activity is assessed against houseflies and mustard beetles by using the following techniques:

Houseflies (*Musca domestica*)

Female flies are treated on the thorax with a one microliter drop of insecticide dissolved in acetone. Two replicates of 15 flies are used at each dose rate and 6 dose rates are used per compound under test. After treatment, the flies are maintained at a temperature of 20°±1° and kill is assessed 24 and 48 hours after treatment. $LD_{50}$ values are calculated in micrograms of insecticide per fly and relative toxicities are calculated from the inverse ratios of the $LD_{50}$ values (see Sawicki et al, Bulletin of the World Health Organisation, 35, 893, (1966) and Sawicki et al, Entomologia and Exp. Appli. 10 253, (1967)).

Mustard beetles (*Phaedon cochleariae Fab*)

Acetone solutions of the test compound are applied ventrally to adult mustard beetles using a micro drop applicator. The treated insects are maintained for 48 hours after which time kill is assessed. Two replicates of 40 to 50 mustard beetles are used at each dose level and 5 dose levels are used for each compound.

$LD_{50}$ values and thence relative potencies are calculated as for houseflies.

For both insect species relative potencies are calculated by comparison with 5-benzyl-3-furylmethyl (IR)-trans-chrysanthemate (Bioresmethrin) which is one of the more toxic chrysanthemate esters known to houseflies and mustard beetle, its toxicity being about 24 times that of allethrin to houseflies and 65 times that of allethrin to mustard beetles.

Results

Relative potencies to Houseflies and Mustard Beetles (Bioresmethrin=100) are given under HF and MB respectively in the Table.

TABLE

Compounds of formula $ArCR_1R_2CR_3{=}CR_4CHDR_B$ (3 POB = 3-phenoxybenzyl; 4F3POB = 4-Fluoro-3-phenoxybenzyl)

| Compound | Ar | $CR_1R_2$ | $R_3$ | $R_4$ | Configuration about double bond | $-CHDR_B$ | HF | MB |
|---|---|---|---|---|---|---|---|---|
| 1 | 4-chlorophenyl | cyclopropyl | H | H | E | 3POB | 53 | 12 |
| 2 | " | " | H | H | E | 4F3POB | 70 | 79 |
| 3 | 4-ethoxyphenyl | cyclopropyl | H | H | E | 3POB | 52 | 58 |
| 4 | " | " | H | H | E | 4F3POB | 100 | 160 |
| 5 | 3,4-methylene dioxyphenyl | cyclopropyl | H | H | E | 3POB | 34 | 15 |
| 6 | 3,4-methylene dioxyphenyl | " | H | H | E | 4F3POB | 77 | 42 |
| 7 | 4-ethoxyphenyl | 2,2-difluoro cyclopropyl | H | H | E | 3POB | — | 42 |
| 8 | " | 2,2-difluoro cyclopropyl | H | H | E | 4F3POB | | 130 |

We claim:
1. A compound of the formula

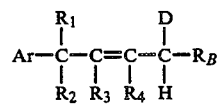

in which:
Ar represents a phenyl or naphthyl group optionally substituted by one or more halogen, alkoxy, haloalkoxy, methylenedioxy, $C_1$–$C_6$ alkyl or haloalkyl groups;

$R_1$ and $R_2$ together with the carbon atom to which they are attached represent a $C_3$–$C_6$ cycloalkyl group optionally substituted by one or more halogen atoms or $C_1$–$C_6$ alkyl groups, $R_3$ and $R_4$, which may be identical or different, represent hydrogen, halogen or $C_1$–$C_6$ alkyl, $R_B$ is phenyl substituted by phenoxy, benzyl or benzoyl, or by fluorine and phenoxy, and D is hydrogen or cyano, the configuration of $ArCR_1R_2$ and $CHDR_B$ about the double bond being mutually trans.

2. A compound according to claim 1, which is substantially free from the isomer of formula II: $ArCR_1R_2CR_3HCR_4=CDR_B$.

3. A compound according to claim 1, in which Ar represent phenyl substituted at the 3-position or 4-position or at both the 3- and 4-positions.

4. A compound according to claim 1, in which Ar is substituted by one or more $C_1$–$C_6$ alkoxy or $C_1$–$C_6$ alkyl groups or halogen or by a methylenedioxyphenyl group.

5. A compound according to claim 4, in which Ar represents phenyl carrying no more than two substituents.

6. A compound according to claim 1, in which Ar represents 4-chlorophenyl or 4-ethoxyphenyl.

7. A compound according to claim 1, in which the cycloalkyl group is substituted or unsubstituted cyclopropyl.

8. A compound according to claim 1, in which $R_3$ and $R_4$ each represent hydrogen.

9. A compound according to claim 1 in which $ArCR_1R_2$ represents 4-chlorophenylcyclopropyl or 4-ethoxyphenylcyclopropyl.

10. A compound according to claim 1, in which D represents hydrogen.

11. 1-(4-chlorophenyl)-1-(E-3-(4-fluoro-3-phenoxyphenyl)-prop-1-enyl)-cyclopropane.

12. 1-(4-ethoxyphenyl)-1-(E-3-(4-fluoro-3-phenoxyphenyl)-prop-1-enyl)-cyclopropane.

13. The compound according to claim 1, wherein $R_B$ is 3-phenoxyphenyl or 4-fluoro-3-phenoxyphenyl.

14. A pesticidal composition useful for combatting pest infestation in domestic, horticultural, agricultural or medical, including veterinary, areas, which comprises a pesticidally effective amount of a compound according to claim 1 in combination with a suitable carrier.

15. A composition according to claim 14, which is substantially free from the isomer II $ArCR_1R_2CR_3HCR_4=CDR_B$.

16. A composition according to claim 14 in the form of a dust, granular solid, wettable powder, mosquito coil, emulsion, emulsifiable concentrate, spray or aerosol.

17. A composition according to claim 14 containing from 0.001 to 25% by weight of the compound of formula I.

18. A composition according to claim 14, in which the compound of formula I is:
1-(4-chlorophenyl-1-(E-3-(4-fluoro-3-phenoxyphenyl)-prop-1-enyl)-cyclopropane, or
1-(4-ethoxyphenyl)-1-(E-3-(4-fluoro-3-phenoxyphenyl)-prop-1-enyl-cyclopropane.

19. A method of pest control, which comprises treating a pest or a surface or environment susceptible to pest infestation with an effective amount of a compound according to claim 1.

20. A method according to claim 19, in which the pest is a rice pest.

21. A method according to claim 19 in which the compound of formula I is:
1-(4-chlorophenyl)-1-(E-3-(4-fluoro-3-phenoxyphenyl)-prop-1-enyl)-cyclopropane, or
1-(4-ethoxyphenyl)-1-(E-3-(4-fluoro-3-phenoxyphenyl)-prop-1-enyl)-cyclopropane.

* * * * *